United States Patent [19]

Fujiu et al.

[11] Patent Number: 5,219,562

[45] Date of Patent: Jun. 15, 1993

[54] HAIR TREATING COMPOSITION

[75] Inventors: Akira Fujiu, Wakayama; Naohisa Kure, Tokyo; Yoshiko Ogura, Chiba, all of Japan

[73] Assignee: Kao Corporation, Tokyo, Japan

[21] Appl. No.: 709,820

[22] Filed: Jun. 4, 1991

[30] Foreign Application Priority Data

Jun. 13, 1990 [JP] Japan ................... 2-154919

[51] Int. Cl.$^5$ .................... A61K 7/06; A61K 7/09
[52] U.S. Cl. ......................... 424/71; 424/70; 568/38; 568/39; 568/55; 568/62
[58] Field of Search ............. 424/70, 71, 401; 568/38, 62

[56] References Cited

U.S. PATENT DOCUMENTS 3,883,598  5/1975  Guthrie ................... 568/62
4,045,472  8/1977  Guthrie ................... 568/62
4,935,230  6/1990  Naito ..................... 424/72

OTHER PUBLICATIONS

*Patent Abstracts of Japan*, vol. 4, No. 98 (C-18) (580) Jul. 15, 1980 and JP-A-55 059 160 (Sankyo Yuki Gosei K.K.) May. 2, 1980.
*Chem. Abst.*, vol. 85, No. 17, Oct. 25, 1976, Columbus, Ohio U.S., abst. no. 123684 P, B. K. Zeinalov et al.: "Synthesis and Study".

*Primary Examiner*—Thurman K. Page
*Assistant Examiner*—Sally Gardner
*Attorney, Agent, or Firm*—Oblon, Spivak, McClelland, Maier & Neustadt

[57] ABSTRACT

A hair treating composition comprising one or more thioglyceryl ethers provides effective wave formation, with a minimized mercapto smell and minimized irritation to the skin.

26 Claims, 2 Drawing Sheets

HAIR TREATING COMPOSITION

BACKGROUND OF THE INVENTION

1. Field of the Invention

The present invention relates to a hair treating composition and more particularly, to a hair treating composition containing a thioglyceryl ether which is excellent in forming hair waves, but which is safe to use and does not possess an offensive odor.

2. Statement of the Prior Art

Heretofore, a variety of mercaptan derivatives have been widely used as the main ingredient in free-radical polymerization controllers, for so-called first agents for cold perm waves, and for cosmetic stabilizers as well as for other uses. However, mercaptan derivatives generally have a very objectionable odor which is a serious drawback when used in consumer products such as treating agents for the modification of hair, e.g., as first agents for forming cold a perm wave. Therefore, there has been and remains a need for mercaptan derivatives which are free of unpleasant odors.

The most common mercaptan derivatives currently being used for cold waving include thioglycolic acid or salts thereof, or cysteine or salts thereof. However, although thioglycolic acid and their salts exhibit excellent sensitivity their strong mercapto odor is quite objectionable even though their hair waving effect is very good. Therefore, attempts have been made to minimize their odor by deodorization treatment through distillation or by admixing with a high masking fragrance. Unfortunately, these techniques have proven to be inadequate. On the other hand, cysteine or salts thereof possess relatively less mercapto and less sensitivity, but are not desirable in that their hair waving ability is insufficient.

The present inventors have previously found that thioglyceryl alkyl ethers and thioglyceryl phenyl ether exhibit an excellent wave-forming effect, are safe and possess minimal objectionable odor (Japanese Patent Application No. 62-20512). However, these compounds still smell bad as compared to conventional thioglycolic acid or salts and their sensitivity is extremely weak.

SUMMARY OF THE INVENTION

It has now been surprisingly found that thioglyceryl ethers represented by formula (I) described below have an excellent wave-forming effect, are safe to use and have only an extremely slight mercapto odor.

The present invention therefore provides a hair treating composition containing a thioglyceryl ether having the following formula (I):

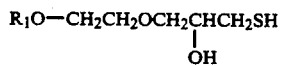

wherein $R_1$ represents a straight or branched chain alkyl group having 1 to 20 carbon atoms or phenyl group.

DETAILED DESCRIPTION OF THE PREFERRED EMBODIMENTS

Figure 1:
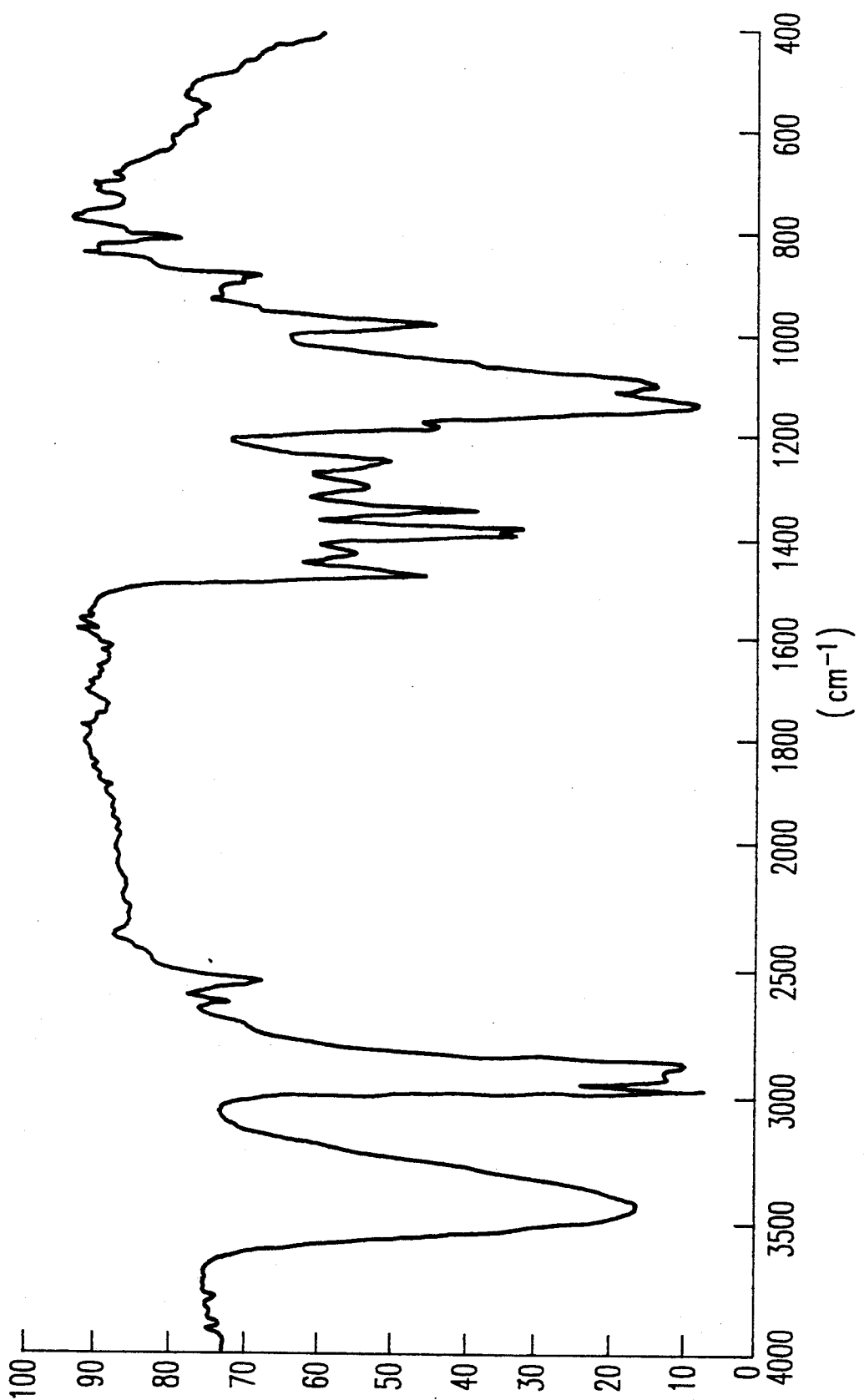
FIG. 1 illustrates an IR absorption spectrum of thioglyceryl isopropoxyethyl ether obtained in Example 1.
Figure 2:
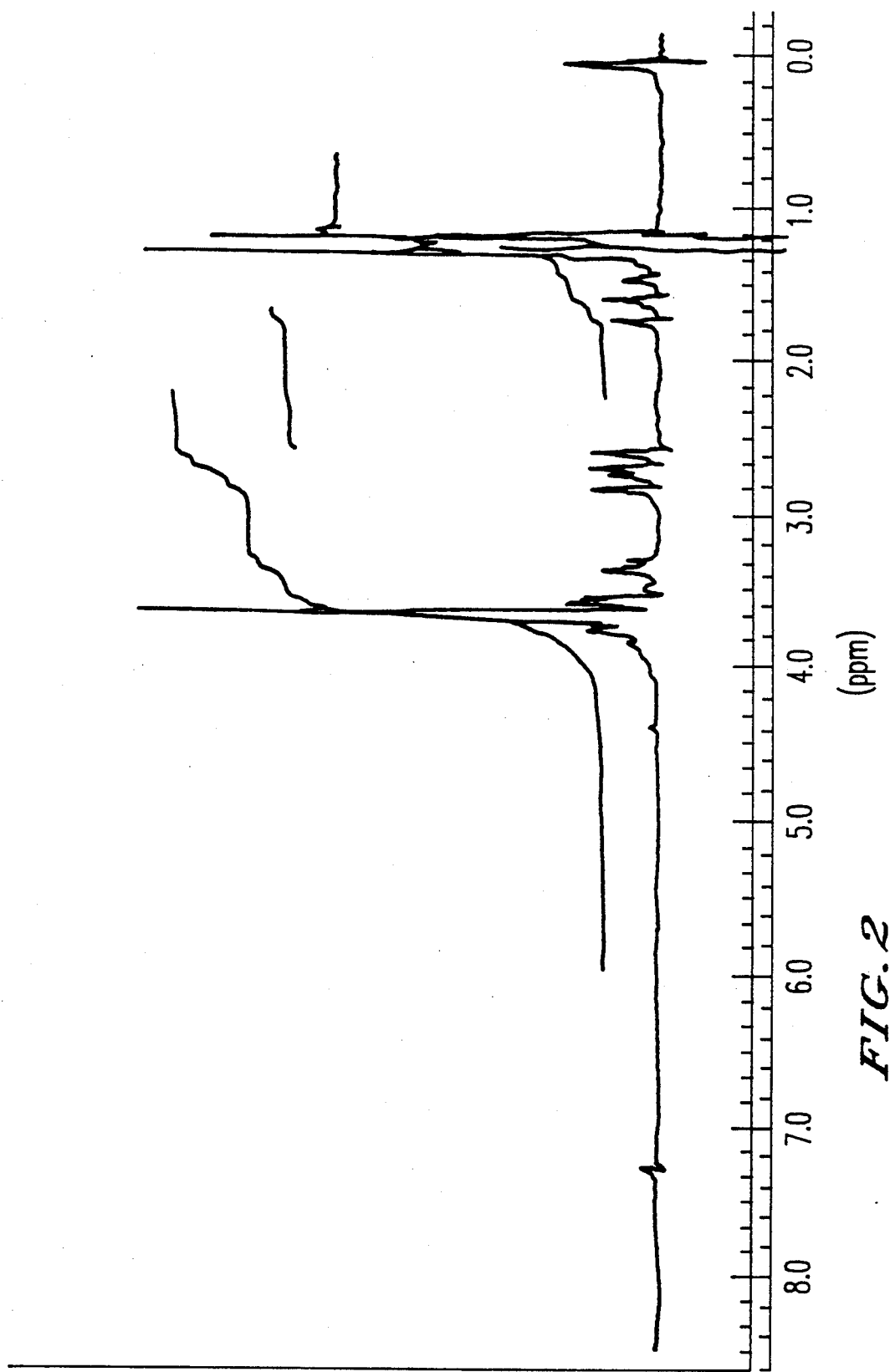
FIG. 2 illustrates an $^1$H-NMR spectrum of thioglyceryl isopropoxyethyl ether obtained in Example 1.

In the thioglyceryl ethers of the formula (I) in accordance with the present invention, specific examples of the straight chain alkyl group shown by $R_1$ include methyl, ethyl, propyl, butyl, pentyl, hexyl, octyl, nonyl, decyl, undecyl, dodecyl, lauryl, myristyl, and stearyl, for example. Specific examples of the branched chain alkyl group include isopropyl, sec-butyl, t-butyl, isopentyl, 2-ethylhexyl, 2-ethyldodecyl, 2-butyldodecyl, for example.

Thioglyceryl ethers wherein $R_1$ represents methyl, ethyl, isopropyl or phenyl are of particular interest in accordance with the present invention.

The thioglyceryl ethers of the present invention may be prepared according to, for example, the following reaction scheme:

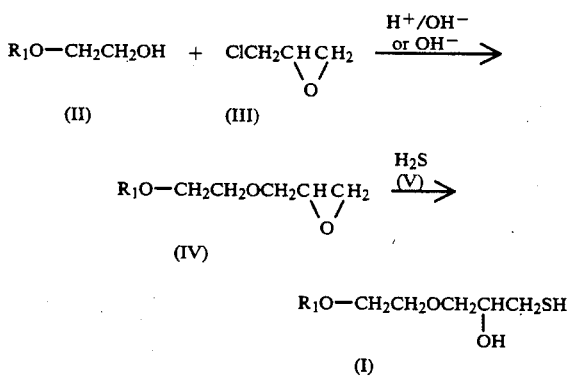

wherein $R_1$ has the same meaning as described above.

That is, the thioglyceryl ethers of the formula (I) may be obtained by reacting an ethylene glycol monoalkyl ether or ethylene glycol monophenyl ether (II) with epichlorohydrin (III) and then reacting the resulting epoxide (IV) with hydrogen sulfide.

The reaction of ethylene glycol monoalkyl ether or ethylene glycol monophenyl ether (II) with epichlorohydrin (III) may be carried out in a conventional manner. For example, the ethylene glycol monoalkyl ether or ethylene glycol monophenyl ether (II) is reacted with epichlorohydrin (III) in the present of an acid catalyst followed by cyclization using an alkali catalyst, Alternatively, these reactants are reacted with each other in one step, using an alkali catalyst alone. Thus, the epoxide (IV) intermediate is obtained. The catalyst may be that as generally used in the reaction of an epoxy group such as an acid catalyst, for example, sulfuric acid; an alkali catalyst, such as sodium hydroxide, potassium hydroxide, or sodium hydride, for example. When an alkali catalyst is used, a quaternary salt may also be present.

The thus obtained epoxide (IV) is purified by distillation, and then reacted with hydrogen sulfide (V) to effect thiolation. The thiolation may be carried out in a conventional manner. By reaction, e.g., epoxide (IV) with hydrogen sulfide (V) in an alcoholic solvent in the presence of a catalyst, the thioglyceryl ether (I) of the present invention is obtained. A lower alcohol such as methanol or ethanol, for example, may be used as the alcoholic solvent. The catalyst, may be a tertiary amine such as triethylamine or the like.

From the thus obtained reaction mixture, amine and solvents are distilled off. Further purification through distillation gives a thioglyceryl ether (I) of high purity.

When the thioglyceryl ether (I) is used as the main ingredient is a hair treating composition, it may be used in the form of first solution in a two bath cold perm waving composition, or in the form of a one bath perm waving composition. In either case, a hair treating composition is obtained which is characterized by high wave-forming efficiency, but which has only a slightly unpleasant odor.

The first solution of the two bath hair treating composition may be prepared by dissolving the thioglyceryl ether (I) in water in an amount of, preferably 1 to 20 wt. % (hereafter simply referred to as %), more preferably 2 to 10%, based on the total amount. It is preferred that the pH of the first solution for the two bath hair treating composition be adjusted with a buffering agent to 4 to 11, preferably 7 to 9.

The one bath hair treating composition may be prepared by dissolving the thioglyceryl ether (I) in water in an amount of, preferably 0.1 to 5.0%, more preferably 0.5 to 3.0%, based on the total amount. It is preferred that the pH of the one bath hair treating composition be adjusted with a buffering agent to 6 to 10, preferably 7 to 9.

Examples of suitable buffering agents include combinations of citric acid/disodium hydrogenphosphate, hydrochloric acid/sodium barbiturate/sodium acetate, hydrochloride acid or maleic acid/trishydroxyaminomethane, potassium dihydrogenphosphate or sodium dihydrogenphosphate/dipotassium hydrogenphosphate or disodium hydrogenphosphate, hydrochloric acid or potassium dihydrogenphosphate or sodium dihydrogenphosphate/sodium tetraborate, potassium dihydrogenphosphate or sodium dihydrogenphosphate/sodium hydroxide or potassium hydroxide, hydrochloric acid/aminomethylpropanediol, glycine/sodium hydroxide or potassium hydroxide, boric acid/sodium hydroxide, hydrochloric acid/sodium dimethylglycine, sodium hydrogencarbonate/sodium carbonate, sodium tetraborate/sodium hydroxide, sodium hydrogencarbonate/sodium hydroxide, water-soluble ammonium salt/ammonia, water-soluble ammonium salt/basic amino acid such as arginine or lysine, for example. Preferred, however, is the combination of water-soluble ammonium salt/ammonia and the combination of water-soluble ammonium/basic amino acid such as arginine or lysine, for example, since the alkali agent does not remain readily on hair, skin, etc. to reduce hair damage and minimize irritation to the skin. The water-soluble ammonium salts such as the hydrochlorides, carbonates and bicarbonates are preferred. These buffering agents may be formulated in the treating composition of the present invention, in an amount of 0.05 to 10%, preferably 0.1 to 5%, in total.

It is preferred to use the hair treating composition of the present invention in combination with at least one of: (i) a peptide or derivatives thereof, (ii) divalent metal salts and (iii) a cationic or amphoteric polymer, for purposes of improving the waving effect, preventing hair damage, and the like.

(i) Peptide or derivatives thereof

Examples include (1) a peptide of at least a dimer synthesized from one or more basic amino acids, e.g., lysine, arginine or a peptide of at least a dimer synthesized from one or more acidic amino acids, e.g., glutamic acid, aspartic acid; (2) keratin protein such as wool, feather or down, a hoof, a horn, etc.; cationated keratin hydrolysate described in Japanese Patent Application Laid-Open No. 57-88111; decomposition derivatives or hydrolysates of proteins such as albumin, globulin, conglutinin or casein, or soybean protein, etc. which are prepared by the method described in Japanese Patent Application Laid-Open No. 57-85308, etc.; (3) natural hormones physiologically active peptides, e.g., insulin, oxidative glutathione, etc. Particularly preferred are polylysine having a molecular weight of 10,000 or less, preferably 5,000 or less; keratin, protein, hydrolysates of soybean protein; and insulin.

These peptides or their derivatives may be formulated in the hair treating composition, either individually or in combination of two or more, in an amount of 0.01 to 50%, preferably 0.1 to 10%.

(ii) Bivalent metal salts

Examples of the divalent metal salts include water-soluble inorganic compounds represented by the following general formula:

$$AB_{2/m}$$

wherein A represents a cation selected from the group consisting of $Ba^{2}$, $Ca^{2+}$, $Zn_{2+}$, $Ni_{2+}$ and $Mg_{2+}$; B represents an anion selected from the group consisting of $F^-$, $Cl^-$, $Br^-$, $I^-$, $SO_4^{2-}$, $PO_4^{3-}$, $OH^-$ and $CO_3^{2-}$; and m represents an atomic valency of B; and organic acid salts such as acetates, citrates, lactates, succinates or tartrates, for example, of the divalent metal (A) described above. Inter alia, acetates or chlorides of calcium, zinc, nickel, magnesium and barium are particularly preferred.

The divalent metal salt may be formulated, by itself or in combination of two or more, in an amount of 10 to 5000 ppm, preferably 100 to 1000 ppm when calculated as metal ions, in the form of final use.

(iii) Cationic or amphoteric polymer

Examples of water-soluble polymers or polymers soluble in water in the presence of inorganic or organic salts, are described in Japanese Patent Application Laid-Open No. 56-92812, and include the following:

(1) Copolymer of acidic vinyl monomer and basic vinyl monomer

As a typical example, mention may be made of an amphoteric polymer obtained by copolymerizing a monomer mixture composed of 45 to 55 mol % of an acidic vinyl monomer or salts thereof and 45 to 55 mol % of a basic vinyl monomer or salt thereof in the presence of a known free radical polymerization initiator or a 150° C. in the presence or absence of a known accelerator. The molar ratio used herein refers to the case where each vinyl monomer contains one acid group or basic group in one molecule. Where a plurality of acidic groups or basic groups are contained in one molecule, the molar ratio will be of course, appropriately adjusted to obtain an approximately zero net charge.

The term "acidic vinyl monomer" means a compound containing an acid group such as carboxyl group, sulfonic acid group or phosphoric acid group, for example, and a polymerizable vinyl group in one molecule. Examples of suitable acidic vinyl monomers include the unsaturated monobasic acids, such as acrylic acid, methacrylic acid, crotonic acid, vinylbenzoic acid, 2-acrylamido-2-methylpropanesulfonic acid, styrenesulfonic acid, vinylsulfonic acid, allylsulfonic acid, methacrylsulfonic acid, or 3-methacrylpropanesulfonic acid, for example, the unsaturated dibasic acids, such as itaconic acid, maleic acid or fumaric acid, for example, or the mono esters thereof. Suitable salts include the sodium salts, potassium salts, ammonium salts, or the like.

The term "basic vinyl monomer" means a compound containing a basic group such as a primary amino group, a secondary amino group or a tertiary amino group, for example, and a polymerizable vinyl group in one molecule. Examples of the basic vinyl monomer include dimethylaminoethyl methacrylate, diethylaminoethyl methacrylate, dimethylaminoethyl, acrylate, diethylaminoethyl acrylate, dimethylaminopropyl, acrylate, dimethylaminopropyl methacrylamide, dimethylaminopropyl acrylamide, 2-vinylpyridine, 4-vinylpyridine or dimethylallylamine, diallylmethylamine, for example; and quaternary compounds thereof. Examples of the quaternary compounds are hydrated, methylated, ethylated compounds, etc. wherein counteranions are halogen ions such as chlorine ions, bromine ions, etc., hydroxy group ions, methyl sulfate group, etc.

(2) Polymer of amphoteric monomer A typical example is an amphoteric polymer obtained by polymerizing an amphoteric monomer represented by the following general formula (VI) at a temperature ranging from 20° to 120° C. in the presence of a radical polymerization initiator.

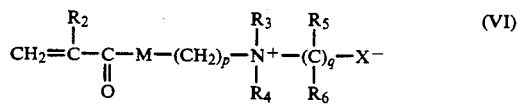

(VI)

in formula (I), $R_2$, $R_5$ and $R_6$ each represents a hydrogen atom or methyl group; $R_3$ and $R_4$ each represents methyl group or ethyl group; M represents —O— or —NH—; X represents —$CO_2$, —$SO_3$ or —$PHO_3$; and p and q each represents an integer of 1 to 3.

The amphoteric monomer represented by formula (VI) can be synthesized by reacting an appropriate aminoalkyl ester or aminoalkylamide of acrylic acid or methacrylic acid with lactone, sulfone or cyclic phosphite.

Examples of these compounds include 3-dimethyl(methacroyloxyethyl)ammonium propanesulfonate, 3-dimethyl(methacroylamidopropyl)ammonium propanesulfonate, etc. dimethyl(methacroylamidopropyl)ammonium propane-sulfonate, etc.

Polymerization may be carried out by a conventionally known manner, for example, mass polymerization, aqueous solution polymerization, reversed phase suspension polymerization, or precipitation polymerization, for example. The reaction proceeds smoothly at a reaction temperature of 20° to 150° C. in the presence of a radical polymerization initiator.

As the radical polymerization initiator, there may be used sodium persulfate, potassium persulfate, ammonium persulfate, 2,2′-azobis(2-amidinopropane)dihydrochloride, benzoyl chloride, hydrogen peroxide, sodium peracetate, cumene hydroperoxide, azobisisobutylonitrile, etc. The amount of the radical polymerization initiator may vary depending upon the type but is preferably about 0.01 to about 5%, based on the total weight of the monomers.

(3) Amino modified silicone polymeric compounds of any molecular structure, e.g., branched, linear, and netting tyupes, can be used as component (B) so long as the same contain in their molecules at least one aminoalkyl group. Organopolysiloxanes which construct the modified silicone polymeric compounds may include, in addition to the above groups, alkyl groups, e.g. methyl, ethyl, propyl; alkenyl groups, e.g. allyl; aryl groups, e.g. phenyl, naphthyl; cycloalkyl groups, e.g. cyclohexyl; hydroxyl, hydroxyalkyl, A typical aminoalkyl group contained in modified silicone polymeric compounds is that shown by the following formula.

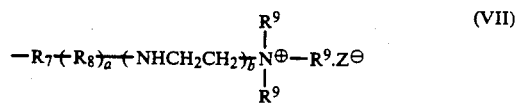

(VII)

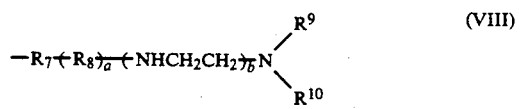

(VIII)

wherein $R_7$ represents a divalent hydrocarbon group, $R_8$ represents a group —$OCH_2CH_2$—,

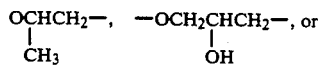

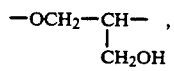

$R_9$ and $R_{10}$ are individually a hydrogen or a monovalent hydrocarbon group, and a and be denote integers of 1–6. $\neq$ represents halogen ion or organic anion.

As divalent hydrocarbon groups represented by $R_7$, alkylene groups, e.g. methylene, ethylene, propylene, butylene, —$CH_2(CH_3)CH_2$—; and alkylene-arylene groups, e.g. —$(CH_2)_2$—$C_6H_4$—, are given. Of these groups, alkylene groups, particularly propylene group, are preferable. Alkyl groups, e.g. methyl, ethyl, propyl, hexyl; and phenyl group are given as examples of monovalent hydrocarbon groups represented by $R_9$ and $R_{10}$. Both $R_9$ and $R_{10}$ may be hydrogen atoms, or both may be monovalent hydrocarbon groups, or either one of $R_9$ and $R_{10}$ is a hydrogen, with the other being a monovalent hydrocarbon group. A preferable value for a and b is 1.

A typical hydroxyalkyl group is shown by the following formula (IX).

(IX)

wherein -$R_7$ has the same meaning as defined above.

Oxylalkylene and polyoxyalkylene groups are typified by the groups shown by the following formula (X).

(X)

wherein -$R_7$ has the same meaning as defined above, c represent 0 or 1, d denotes an integer of 1–100, and e is indicates an integer of 1–5.

Of the hydroxyalkyl groups represented by formula (X), those in which c=1, d=3 to 70, and e=2 or 3 are preferable. A hydroxyalkyl group produced by random or block bond of a group having the value e=2 and a group having the value e=3 is acceptable. This applies to the cases where e is other than 2 or 3.

Typical amino modified silicone polymeric compounds are those represented by formulae (XI) and (XII).

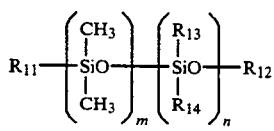
(XI)

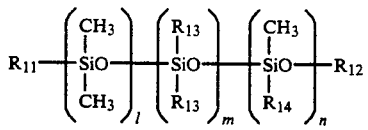
(XII)

wherein $R_{11}$ is a methyl or hydroxy group, and $R_{12}$ is a methyl group or a hydrogen, $R_{13}$ is above-mentioned aminoalkyl group (VII) or (VIII), $R_{14}$ is a hydroxy, hydroxyalkyl, oxyalkylene, or polyoxyalkylene group, and l, m and n are integers dependent on the molecular weight.

Of these, particularly preferable amino modified silicone polymeric compounds are those represented by formula (XIII).

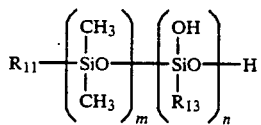
(XIII)

wherein $R_{13}$ is above-mentioned aminoalkyl group (VII) or (VIII), and l, m and n are integers dependent on the molecular weight.

One of the specific examples of amino modified silicone polymeric compounds is that described in the Cosmetic Ingredient Dictionary, third edition, having the name of

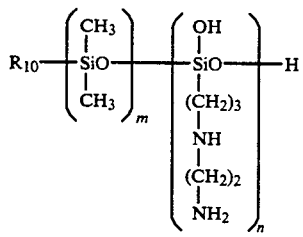
(XIV)

wherein m and n are integers dependent on the molecular weight.

It is desirable that the amino modified silicone polymeric compounds of the present invention be used in a form of aqueous emulsion. Such an emulsion can be obtained by emulsifying, in the presence of a quarternary ammonium salt surfactant and water, a cyclic diorganopolysiloxane and an organodialkyoxysilane having an aminoalkyl group and at least one group selected from hydroxyl, hydroxylalkyl, oxyalkylene, and polyoxyalkylene groups, according to the process described, for example, in Japanese Patent Application Laid-Open No. 38609/1981.

When the amino modified silicone polymeric compounds is used in a form of aqueous emulsion, the amount of modified silicone polymeric compounds in the emulsion is usually 20–60% by weight, and preferably 30–50% by weight.

Given as examples of commercial modified silicone polymer emulsions which can be suitable used in this invention are SM 8702C (tradename, product of Toray Silicone Co.) and DC 929 (tradename, product of Dow Coaning Co.), both being Amodimethicone.

These cationic or amphoteric polymers are used alone or in combination of two or more, in the formulation of the treating composition for modifying hair, in an amount of 0.01 to 20%, preferably 0.1 to 10%.

The treating composition for modifying hair of the present invention may further contain conventionally known components within such a range that they do not interfere the effect of the present invention. Examples of the other components include higher alcohols; cationic, anionic and amphoteric surfactants; urea silicone; aluminum compounds such as aluminum stearate, alum, etc.; organic acids such as citric acid, malic acid, etc.; ethylenediamine, mono-, di- or triethanolamine, aminohydroxymethylpropanediol, 2-amino-2-methyl-1-propanol, 2-amino-2-methyl-1,3-propanediol, morpholine; basic amino acids such as arginine, lysine, etc.; alkali agents such as ammonia, sodium hydroxide, etc.; and hair tonic, sterilizers, coloring matters, fragrance, etc.

Where the treating composition for modifying hair of the present invention is used as a first solution for two bath cold permanent waving composition, a conventional solution is used as a second solution followed by permanent waving treatment in a conventional manner. Where the composition is used as a permanent waving agent for warming mono bath permanent waving composition, permanent wave treatment is carried out by the following method. That is, the treating agent is applied to hair. It is desired that prior to application of the treating agent, the hair be wound around rods, curlers, a heatable handy setting equipment, etc. to form a desired loose wave. However, where it is desired to form a loose wave, hair may be finished dressed by blowing wit a drier, a brush, etc. The amount of the composition to be applied may vary depending upon the conditions of temperature for warming, etc. but is generally preferably in a range of 10 to 150 ml per one time. Then, the hair is heated to 40° to 160° C. The actual temperature and time of heating may vary depending upon the degree of hair damage, the type of peptide used, the type of buffering agent, the pH, the form of treating agent, etc. It is advantageous that normal hair which is not permed, dyed or bleached be treated at a high temperature. Taking into account hair damage caused by heating, however, it is preferred to effect treatment at a temperature between 40° to 160° C., especially 40° and 80° C. It is even more effective to cover the hair with a cap and further moisten the hair upon heating, so as not to vaporize moisture from hair. The heating time should be longer as the temperature is reduced. For the same reason, however, a shorter time period of less than 30 minutes, especially 3 to 10 minutes, is preferred. On the other hand, it is desired to choose milder conditions for treating chemically treated hair such as perming, hair dyeing, bleaching, etc.

The thioglyceryl ethers of the present invention may also be used as an antioxidant, a stabilizer, or the like treating all types of hair, or can be formulated into hair cosmetics. For example, where the thioglyceryl ether is formulated in the first agent for oxidation hair dye composition, the thioglyceryl ether will prevent autoxidation of the color developer and the coupler material, so that a keratin fiber dyed composition having excellent stability can be obtained. Furthermore, where the thioglyceryl ether is formulated into a shampoo, a rinse, a treatment agent, a blowing agent, a hair set composition or the like, the thioglyceryl ether can prevent coloration of these agents or compositions and change in liquid nature so that a composition having excellent stability during storage can be obtained.

Where the present thioglyceryl ethers are used for hair treating agents other than the treating composition for modifying hair or for hair cosmetics, the thioglyceryl ether is formulated in an amount of preferably 0.01 to 10.0%, more preferably 0.05 to 5.0%, based on the total amount.

The thioglyceryl ethers of the present invention may also be used as a polymerization regulator (TELOGEN) for radical polymerization.

The thioglyceryl ethers of the present invention are mercaptan derivatives which have minimized irritation and less odor. The thioglyceryl ethers of the present invention may be advantageously used as a polymerization regulator (TELOGEN) for free radical polymerization. In addition, where the thioglyceryl ethers are used as the main ingredient for the treating composition for modifying hair as described above, the treating composition for modifying hair which provides a better wave forming effect and has a less offensive odor can be provided, as compared to conventional treating agents using as the main ingredient thioglycolic acid or a salt thereof. By formulating the thioglyceryl ether in the hair treating composition and hair cosmetics as an antioxidant and stabilizer, the hair treating composition a hair cosmetic composition having excellent stability may be provided.

In general, the conventional solution used as a second solution for a two bath cold permanent waving composition contains from 0.5 to 20 wt. % of an oxidation agent. The oxidation agents may include bromic acid, perboric acid or a salt thereof, hydrogen peroxide or iodine, for example. For example, a second solution as disclosed in U.S. Pat. No. 3,865,930 may be used, which patent is incorporated herein in the entirety.

A variety of additives may be added to the second solution in order to reduce hair damage by perm treatment or to enhance finish feeling. For example, the water-soluble polymers of U.S. Pat. No. 4,027,008, amidimethicone of U.S. Pat. No. 4,770,873, cationic dextran derivatives of U.S. Pat. No. 4,426,375, citric acid or salts thereof of U.S. Pat. No. 4,349,537 and water-soluble keratin hydrolyzates of U.S. Pat. No. 4,232,123 may be added. Each of the patents described above in this paragraph are also incorporated herein in the entirety.

Further, as noted above, about 10 ml to 150 ml of composition is applied for the warming mono bath method. For the cold two bath method, the amount of composition to be applied may vary depending upon the length of hair, or whether a partial perm or an entire perm is desired. However, in general, about 10 ml to 200 ml is used.

Generally, for the warming mono bath method, the amount of composition used may be from about 10 ml to 300 ml, but preferably from about 10 ml to 150 ml. The treating time is about 0.5 to 30 minutes, but preferably from 3 to 10 minutes. The temperature is from about 40° to 160° C., but preferably from 40° to 80° C.

Additionally, when using the warming mono bath method, the following general composition is used:

| Composition | wt. % |
| --- | --- |
| thioglyceryl ether | 0.1–5 |
| buffering agent | 0.05–10 |
| peptide or its derivative | 0.01–50 |
| salt of divalent metal | 10–5000 ppm (metal ion) |
| cationic or amphoteric polymer | 0.01–10 |
| surfactant | 0.1–20 |
| chelating agent (sequestrant) | 0.1–2 (pH 6–10) |

When using the cold two bath method, for the application of the first solution, a treating time of about 2 to 30 minutes is used, but preferably about 5 to 15 minutes. A composition amount of about 10–300 ml, but preferably about 10–200 ml is used. The temperature used is ambient.

Further, when using the cold two bath method, the following general composition is used:

| Composition | wt. % |
| --- | --- |
| thioglyceryl ether | 1–20 |
| buffering agent | 0.05–10 |
| peptide or its derivative | 0.01–50 |
| salt of divalent metal | 10–5000 ppm (metal ion) |
| cationic or amphoteric polymer | 0.01–10 |
| surfactant | 0.1–20 |
| chelating agent | 0.1–2 (pH 4–11) |

The invention will now be further described by reference to certain examples which are provided solely for purposes of illustration and are not intended to be limitative.

EXAMPLE 1

In a reaction flask equipped with a stirrer, a thermometer and a reflux condenser, 832 g (8 mols), 24 g of strongly acidic resin (NAFION H: Du Pont Co., Ltd.) and 370 g (4 mols) of epichlorohydrin were stirred at 80° C. for 4.5 hours. The reaction mixture was ice-cooled. After NAFION H was recovered, the filtrate was distilled to give 620 g of the halohydrin compound (5 to 20 mmHg/45 to 50° C.).

The halohydrin compound previously obtained was charged in a reaction flask equipped with a stirrer, a thermometer and a reflux condenser and reacted with 472 g (5.4 mols) of 46% sodium hydroxide aqueous solution at 30° C. for 4 hours. After the formed sodium chloride was removed, the system was washed with water and distilled to give 225,5 g of the epoxide (120° to 125° C./68 to 75 mmHg).

In a reactor equipped with a stirrer, a thermometer, a reflux condenser and a gas feeding tube, 832 g (8 mols), 440 g of ethanol and 46.3 g of triethylamine was charged and hydrogen sulfide gas was then introduced. After it was verified that the inside of the reactor was saturated with hydrogen sulfide gas, 220 g (1.375 mol) of the epoxide was reacted with hydrogen sulfide at 10° C. until absorption of hydrogen sulfide was not noted (about an hour). After replacing to give 270.4 g of the crude product.

The crude product was distilled to give 156 g of the desired thioglyceryl isopropoxyethyl ether (122° to 125° C./5 to 7 mmHg).

SH content: more than 99%; purity by gas chromatography (GC): more than 99%.

The results of analysis and identification of this compound are as follows.

Mass spectrometry (GC/MS method)

m/e 194 was detected. This signal corresponds to the signal of the parent ion of thioglyceryl isopropoxyethyl ether.

| IR (cm$^{-1}$, neat method) | |
|---|---|
| 3442 | OH stretching vibration |
| 2638, 2560 | SH stretching vibration |
| 1128, 1092 | C—O stretching vibration |
| $^1$H-NMR (δ ppm CHCl$_3$) | |
| 2.7 | hydrogen from methylene at the α-position of SH |
| 1.6 | hydrogen of SH |
| 1.2 | hydrogen of dimethyl in isopropoxy |

Elemental Analysis (as $C_8H_{18}O_3S$):
Found (%) C 49.48, H 9.28, 0 24.74, S 16.49.
Cald. (%) C 49.15, H 9.78, 0 24.38, S 16.24.

From the above results, this compound is identified as thioglyceryl isopropoxyethyl ether.

EXAMPLES 2 THROUGH 4

Various thioglyceryl ethers were obtained in a manner similar to Example 1, except that methoxyethanol, ethoxyethanol and phenoxyethanol were used, respectively, in place of isopropoxyethyl in Example 1. Conditions for synthesis and results are summarized in Table 1.

TABLE 1

| | | Raw Material/Amount Charged (g) | | Yield (g)* | Purity | |
|---|---|---|---|---|---|---|
| Ex. | Alcohol | Epichloro-hydrin | Intermediate epoxide | Final thiol derivative | SH Content (%) | GC Purity (%) |
| 2 | Methoxyethanol 900 | 490 | 268 | 251 | ≧99 | ≧99 |
| 3 | Ethoxyethanol 912 | 589 | 278 | 196 | ≧99 | ≧99 |
| 4 | Phenoxyethanol 1140 | 258 | 258 | 229 | ≧99 | ≧99 |

*Yield after distillation

Analysis of the thioglyceryl ethers obtained as the final products afforded results which are summarized in Tables 2 and 3.

TABLE 2

| Mass spectrometry | |
|---|---|
| Example | m/e |
| 2 | 166 |
| 3 | 180 |
| 4 | 228 |

TABLE 3

| Example | | Elemental analysis | | | | |
|---|---|---|---|---|---|---|
| | | C | H | O | S | |
| 2 | Found (%) | 43.37 | 8.43 | 28.92 | 19.28 | $C_6H_{14}O_3S$ |
| | Cald. (%) | 43.40 | 8.26 | 28.78 | 19.19 | |
| 3 | Found (%) | 46.67 | 8.89 | 26.67 | 17.78 | $C_7H_{16}O_3S$ |
| | Cald. (%) | 46.61 | 8.78 | 26.72 | 17.54 | |
| 4 | Found (%) | 57.89 | 7.02 | 21.05 | 14.04 | $C_{11}H_{16}O_3S$ |
| | Cald. (%) | 57.69 | 6.89 | 21.22 | 13.86 | |

With respect to all of the thioglyceryl ethers obtained in Example 2 through 4, SH stretching vibration was confirmed by IR (cm$^{-1}$, neat): 2500–2700 cm$^{-1}$. Furthermore, hydrogen of SH and hydrogen of methylene at the α-position of SH were observed by $^1$H-NMR (δppm, CDCl$_3$): 1–3 ppm.

From the foregoing results, the compounds obtained in Examples 2 through 4 were identified as thioglyceryl methoxyethyl ether, thioglyceryl ethoxyethyl ether and thioglyceryl phenoxyethyl ether, respectively.

EXAMPLE 5

With respect to the thioglyceryl ethers obtained in Examples 1 through 4, the smell of the stock solutions was evaluated by a perfumer. The results are shown in Table 4.

Criterion for evaluation
- ⊙ hardly smells
- ◯ somewhat smells
- Δ somewhat strongly smells
- X strongly smells

TABLE 4

| Thioglyceryl Ether | Evaluation of Smell by Perfumer |
|---|---|
| This Invention: | |
| Thioglyceryl methoxyethyl ether | ◯ |
| Thioglyceryl ethoxyethyl ether | ◯ |
| Thioglyceryl isopropoxyethyl ether | ⊙ |
| Thioglyceryl phenoxyethyl ether | ◯ |
| Comparison: | |
| Thioglycolic acid | Δ |
| Thioglyceryl ethyl ether | Δ |

EXAMPLE 6

First solutions for cold perm waving agent having the following compositions containing the present thioglyceryl ethers obtained in Examples 1 through 4 or thioglycolic acid (comparative compound) were prepared. Using a normal hair wig, the wig was subjected to a cold perm treatment (first solution—10 minutes, room temperature; second solution—10 minutes, room temperature to evaluate the ability of wave forming and the smell generated during the process of application, by beauticians. The results are shown in Table 5.

| First solution: | |
|---|---|
| Thioglyceryl ether | 5.0% |
| EDTA | 0.5% |
| Ammonium bicarbonate | 3.0% |
| Water, ammonia | |
| (pH was adjusted to 9.0 with ammonia) | |
| Second solution: | |
| Sodium hydrobromide | 5.0% |
| Water | 95.0% |

| Criterion for evaluation: | | | |
|---|---|---|---|
| Ability of forming wave | | Smell upon application | |
| ⊙ | strong | ⊙ | hardly smells |
| ◯ | somewhat strong | ◯ | somewhat smell somewhat |
| Δ | somewhat weak | Δ | strongly smell |
| x | weak | x | strongly smell |

TABLE 5

| Thioglyceryl Ether | Ability of Forming Wave | Evaluation of Smell |
| --- | --- | --- |
| This Invention: | | |
| Thioglyceryl methoxylated ether | ◉ | ◉ |
| Thioglyceryl ethoxylated ether | ◉ | ◉ |
| Thioglyceryl isopropoxymethyl | ◉ | ◉ |
| Thioglyceryl phenoxyethyl ether | ◉ | ◉ |
| Comparison: | | |
| Thioglycolic acid | ○ | △ |

EXAMPLE 7

Warming type mono bath permanent waving agents having the following compositions using the thioglyceryl ethers obtained in Examples 1 through 4 were prepared and the ability of forming wave was examined. The results are shown in Table 6.

| Mercapto compound | % (Table 6) |
| --- | --- |
| EDTA | 0.5% |
| Disodium phosphate.12 hydrate | 3.0% |
| Water | balance |
| Sodium hydroxide (ph was adjusted to 8.0 with sodium hydroxide) | |

METHOD OF MEASURING DEGREE OF WAVING

Ten strands of Japanese normal hair of 15 cm in length were formed in a bundle. The bundle was wound around a glass tube (10 mm in diameter) and immersed in each treating composition at 50° C. and 80° C., respectively, for 15 minutes. After thoroughly rinsing with water, the bundle of hair was withdrawn from the glass tube and hair became like coil. A length of the hair coil at this time was measure.

Waving degree was determined according to the following equation.

$$\text{Waving degree (\%)} = \frac{Y}{X - Y} \times 100$$

X: full length of hair (15 cm)
Y: length of hair coil (cm)

TABLE 6

| Mercapto compound Of the Present Invention: | Amount formulated (%) | Treating temperature (°C.) | Waving Degree (%) |
| --- | --- | --- | --- |
| Thioglyceryl methoxyethyl ether | 3.3 | 50 | 35 |
| | | 80 | 54 |
| Thioglyceryl ethoxyethyl ether | 3.6 | 50 | 34 |
| | | 80 | 52 |
| Thioglyceryl isopropoxyethyl ether | 3.9 | 50 | 36 |
| | | 80 | 57 |
| Thioglyceryl phenoxyethyl ether | 4.6 | 50 | 32 |
| | | 80 | 52 |

Having described the present invention, it will now be apparent to one of ordinary skill in the art that many changes and modifications can be made to the embodiments described above without departing from the spirit and the scope of the present invention.

What is claimed as new and desired to be secured by letters patent of the United States is:

1. A thioglyceryl ether having the formula (I):

$$R_1O-CH_2CH_2OCH_2CHCH_2SH \quad (I)$$
$$|$$
$$OH$$

wherein $R_1$ represents a straight or branched chain alkyl group having 1 to 20 carbon atoms or phenyl group.

2. The thioglyceryl ether of claim 1, wherein $R_1$ represents a methyl, ethyl, isopropyl or phenyl group.

3. A composition suitable for use as a first solution for a two bath cold permanent wave hair treatment, which comprises an amount of at least one thioglyceryl ether effective for forming hair waves having the formula (I):

$$R_1O-CH_2CH_2OCH_2CHCH_2SH \quad (I)$$
$$|$$
$$OH$$

wherein $R_1$ represents a straight or branched chain alkyl group having 1 to 20 carbon atoms or phenyl group; and water.

4. The composition of claim 3, wherein said composition contains from about 1 to 20 wt. % of said at least one thioglyceryl ethers.

5. The composition of claim 4 wherein said composition contains from about 2 to 10 wt. % of said at least one thioglyceryl ethers.

6. The composition of claim 3, which further contains a buffering agent effective to adjust the pH of said composition to about 4 to 11.

7. The composition of claim 6, wherein said buffering agent adjusts the pH of said composition to about 7 to 9.

8. A composition suitable for use as a one bath warming permanent wave hair treatment composition, which comprises from about 0.1 to 5.0 wt. % of at least one thioglyceryl ether having the formula (I):

$$R_1O-CH_2CH_2OCH_2CHCH_2SH$$
$$|$$
$$OH$$

wherein $R_1$ represents a straight or branched chain alkyl group having 1 to 20 carbon atoms or phenyl group; and water.

9. The composition of claim 8, wherein said composition contains from about 0.5 to 3.0 wt. % of said at least one thioglyceryl ethers.

10. The composition of claim 8, which further contains a buffering agent effective to adjust the pH of said composition to about 6 to 10.

11. The composition of claim 10, wherein said buffering agent adjusts the pH of said composition to about 7 to 9.

12. The composition of claim 3, which further contains an effective amount of at least one of: i) at least one divalent metal salt, and ii) at least one cationic or amphoteric polymer, which is water-soluble or water-soluble in the presence of inorganic or organic salts.

13. The composition of claim 12, which further contains at least one peptide or derivative thereof in an amount of about 0.01 to 50% by weight.

14. The composition of claim 12, wherein said at least one divalent metal salt are used in an amount of about 10 to 5,000 ppm.

15. The composition of claim 12, wherein said at least one cationic or amphoteric polymer are used in an amount of about 0.01 to 20% by weight.

16. The composition of claim 8, which further contains an effective amount of at least one of: i) at least one divalent metal salt, and ii) at least one cationic or amphoteric polymer.

17. The composition of claim 16, which further contains at least one peptide or derivative thereof in an amount of about 0.01 to 50 % by weight.

18. The composition of claim 16, wherein said divalent metal salts are used in an amount of about 10 to 5,000 ppm.

19. The composition of claim 16, wherein said at least one cationic or amphoteric polymer are used in an amount of about 0.01 to 20% by weight.

20. A method for treating hair for effecting cold permanent waving, which comprises:
    a) applying to said hair, a first solution which comprises an effective amount of at least one thioglyceryl ether of the formula (I):

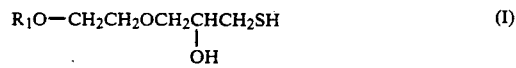

wherein $R_1$ represents a straight or branched chain alkyl group having 1 to 20 carbon atoms or phenyl group,
    b) treating said hair with a second solution comprising sodium hydrobromide and water, and
    c) subjecting said treated hair to permanent waving treatment.

21. The method of claim 20, wherein $R_1$ represents methyl, ethyl, isopropyl or phenyl.

22. A method for effecting warming permanent waving of hair, which comprises:
    a) applying to said hair, a first solution which comprises a hair waving effective amount of one or more thioglyceryl ethers of the formula (I):

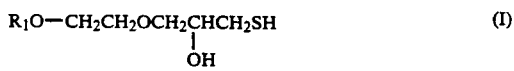

wherein $R_1$ represents a straight or branched chain alkyl group having 1 to 20 carbon atoms or phenyl group, and
    b) heating said hair to a temperature effective for effecting permanent waving of said hair.

23. The method of claim 22, wherein said hair is heated to about 40° to 160° C.

24. The method of claim 23, wherein said hair is heated to about 40° to 80° C.

25. The method of claim 23, wherein said heating is effected for a period of less than about 30 minutes.

26. The method of claim 25, wherein said heating is effected for a period of about 3 to 10 minutes.

* * * * *